(12) United States Patent
Chapelon et al.

(10) Patent No.: US 10,004,888 B2
(45) Date of Patent: Jun. 26, 2018

(54) METHOD FOR DETERMINING OPTIMIZED PARAMETERS OF A DEVICE GENERATING A PLURALITY OF ULTRASOUND BEAMS FOCUSED IN A REGION OF INTEREST

(71) Applicant: (INSERM) INSTITUT NATIONAL DE LA SANTE ET DE LA RECHERCHE MEDICALE, Paris (FR)

(72) Inventors: Jean-Yves Chapelon, Villeurbanne (FR); Cyril Lafon, Toussieu (FR); Jean-Louis Mestas, Veyrins-Thuellin (FR)

(73) Assignees: INSTITUT NATIONAL DE LA SANTÉ ET DE LA RECHERCHE MÉDICALE (INSERM), Paris (FR); UNIVERSITE CLAUDE BERNARD, Villeurbanne (FR); CENTRE LÉON BÉRARD, Lyons (FR)

( * ) Notice: Subject to any disclaimer, the term of this patent is extended or adjusted under 35 U.S.C. 154(b) by 0 days. days.

(21) Appl. No.: 14/383,805

(22) PCT Filed: Mar. 8, 2013

(86) PCT No.: PCT/EP2013/054718
§ 371 (c)(1),
(2) Date: Sep. 8, 2014

(87) PCT Pub. No.: WO2013/132060
PCT Pub. Date: Sep. 12, 2013

(65) Prior Publication Data
US 2015/0141734 A1 May 21, 2015

(30) Foreign Application Priority Data
Mar. 8, 2012 (EP) .................................... 12305278

(51) Int. Cl.
*A61H 1/00* (2006.01)
*A61M 37/00* (2006.01)
(Continued)

(52) U.S. Cl.
CPC ......... *A61M 37/0092* (2013.01); *A61B 18/04* (2013.01); *A61D 1/00* (2013.01);
(Continued)

(58) Field of Classification Search
CPC .............................. A61N 7/00; A61H 23/0245
See application file for complete search history.

(56) References Cited

U.S. PATENT DOCUMENTS

| 5,501,655 A | * | 3/1996 | Rolt | A61N 7/02 600/439 |
| 6,428,532 B1 | | 8/2002 | Doukas et al. | |
| 2011/0270075 A1 | * | 11/2011 | Vitek | A61N 7/02 600/411 |

FOREIGN PATENT DOCUMENTS

| WO | 2008018019 A2 | 2/2008 |
| WO | 2008143998 A1 | 11/2008 |
| WO | 2009045411 A2 | 4/2009 |

OTHER PUBLICATIONS

International Search Report dated Jun. 6, 2013 re: PCT/EP2013/054718; citing: U.S. Pat. No. 6,428,532 B1, WO 2008/143998 A1, U.S. Pat. No. 5,501,655 A and WO 2009/045411 A2.

* cited by examiner

*Primary Examiner* — Hien Nguyen
(74) *Attorney, Agent, or Firm* — Cantor Colburn LLP (57) ABSTRACT

The method determines parameters to generate confocal ultrasound beams (B1,B2) inside a medium (4), and uses a device (1) comprising first and second ultrasound means (11,12) and first and second displacement members (13,14) for moving the ultrasound means (11,12). The parameters (Continued)

include signals s1,s2 to the ultrasound means (11,12), and the positions x1,x2 of the ultrasound means (11,12). The parameters are optimized for having a minimum amplitude a1,a2 of the signals s1,s2 and having an acoustic effect inside the medium (4).

22 Claims, 4 Drawing Sheets

(51) Int. Cl.
    *A61N 7/02*     (2006.01)
    *A61B 18/04*     (2006.01)
    *A61D 1/00*     (2006.01)
    *A61D 7/00*     (2006.01)
    *A61N 5/10*     (2006.01)
    *G10K 11/35*     (2006.01)
    *A61N 7/00*     (2006.01)
    *A61B 18/00*     (2006.01)
    *A61B 90/00*     (2016.01)

(52) U.S. Cl.
    CPC .............. *A61D 7/00* (2013.01); *A61N 5/1001* (2013.01); *A61N 7/02* (2013.01); *G10K 11/352* (2013.01); *A61B 2018/00577* (2013.01); *A61B 2018/00994* (2013.01); *A61B 2090/0472* (2016.02); *A61M 2037/0007* (2013.01); *A61N 2007/0008* (2013.01); *A61N 2007/0039* (2013.01); *A61N 2007/0091* (2013.01); *A61N 2007/0095* (2013.01)

METHOD FOR DETERMINING OPTIMIZED PARAMETERS OF A DEVICE GENERATING A PLURALITY OF ULTRASOUND BEAMS FOCUSED IN A REGION OF INTEREST

TECHNICAL FIELD

The present invention concerns a method for determining optimized parameters of a device generating a plurality of ultrasound beams which are focused on a focal point P situated in a region of interest which can be a region inside a medium or a region at the interface between a first and a second fluid of the medium.

INTRODUCTION

According to the present invention, the medium may be any medium that can propagate ultrasound waves. For example, the medium may be an aqueous medium. The medium may be a human or animal body. The medium may be also an aqueous medium enclosed inside a test tube or a test capsule or any test device. Therefore, the medium may be an in-vitro or an in-vivo medium.

According to the present invention, "a region of interest" means a region which has a size in all directions lower than 5 mm, and preferably lower than 2 mm. This region of interest can be inside a tumor, in particular a cancer tumor, inside an animal or a human body or it can be cells stored in a medium such an aqueous medium or any culture medium. The medium may be a culture medium used for in-vitro experiments on substances of interest before the carrying out of the experiments in in-vivo conditions.

According to the present invention, the wording "a device generating a plurality of ultrasound beams which are focused on a focal point P situated in a region of interest" means that the device produces around the focal point P inside the region of interest at least one effect chosen amongst:
- a cavitation effect localized inside the region of interest localized inside the medium,
- a single acoustic fountain effect localized in the region of interest which is at the interface between a first and a second fluid of the medium,
- a thermal increase effect localized inside the region of interest inside the medium.

According to the method, the device generates a localized ultrasound intensity or in other words it generates a localized ultrasound pressure around the focal point P in the region of interest.

According to the present of the invention, the wording "optimized parameters of a device generating a plurality of ultrasound beams which are focused on a focal point P situated in a region of interest" are the parameters of amplitude of the signals and the positions to each other of the means generating said ultrasound beams.

BACKGROUND

The medium is susceptible to the cavitation phenomenon. The cavitation is the creation or formation of vapor bubbles in a medium in a region where the pressure falls below a pressure threshold, said threshold corresponding to the called cavitation level. Additionally, said pressure threshold may be the vapor pressure of said medium or higher to this vapor pressure. During cavitation, the cavitation bubbles may dynamically oscillate. Then, the cavitation bubbles may rapidly collapse, producing a localized shock wave in the medium, an increase of local temperature, some mechanical stresses and/or chemical effects. The cavitation may be produced when the medium comprises some nuclei. The cavitation may be also produced by adding microbubbles or bubbles inside the medium, or by adding ultrasound contrast agents.

Moreover, it is well-known to use ultrasound waves for delivering a substance inside a region of interest. More precisely, it is known to generate and to focus a single ultrasound beam on a point inside a medium (i.e. a target point), so that to produce cavitation inside a region around said target point and to make a delivery compound to switch from a holding state in which the substance is held by the delivery compound, to a releasing state in which the substance is released by the delivery compound.

The substance may be a chemical substance, a radioactive substance, a color substance, a gene, a plasmide or a drug. The substance may be held by a delivery compound in a holding state when there is no cavitation inside the medium in near proximity of the delivery compound. In that state, the substance is not free to move into the medium independently of the delivery compound, and is not able to be active and to react with another substance inside the medium. The substance is released by the delivery compound in a releasing state when there is cavitation inside the medium in near proximity of the delivery compound. In that state, the substance is free to move into the medium independently of the delivery compound, and is able to be active and to combine with other substance.

The delivery compound is therefore sensitive to the cavitation, and releases the substance if it is in near proximity of cavitation bubbles. Near proximity means a distance between the delivery compound and a cavitation bubble smaller than 1 mm. If cavitation bubbles are localized inside a region of interest of the medium, i.e. if the cavitation occurs inside said region of interest, the delivery compound releases the substance substantially inside said region of interest. The substance is transported through the medium to the localized region of interest inside said medium and is released inside said localized and reduced region of interest. The delivery compound may be considered as a means of transportation and delivering for the substance inside the medium from any origin to the localized region of interest. Many delivery compounds are well-known. It may be a microparticules or nanoparticle, and for example a liposome, a micelle, or the like.

In another case, the substance may be released without a delivery compound inside a region of interest of the medium when there is cavitation inside said region of interest of the medium. Indeed, the substance may be sensitive to the cavitation.

As used herein, the term "particles" refers to an aggregated physical unit of solid material. The particles according to the invention may be micro- or nanoparticles. Microparticles are understood as particles having a median diameter d50 ranging from 500 µm to 1 µm and more preferably from 100 µm to 1 µm, and most preferably from 10 µm to 1 µm. Nanoparticles are understood as particles having a median diameter d50 inferior to 1 µm and notably ranging from 0.1 µm and 0.01 µm. As used herein, the term "median diameter d50" refers to the particle diameter so that 50% of the volume or of the number of the particles population have a smaller diameter. More specifically, the microparticles or nanoparticles may be microspheres or microcapsules, nanospheres or nanocapsules respectively, containing an active substance.

In particular, the generation of ultrasound intensity (i.e. ultrasound pressure) localized in a region of interest, for example a cancer tumor is well-known and very interesting. Indeed, it may be used for drug delivering inside a body. The body is for example an animal or a human body. The drug may be delivered inside the body preferentially to a predetermined region inside the body (i.e. the "region of interest"), and less somewhere else. Moreover, the needed quantity of drug for the treatment of the predetermined region is greatly reduced compared to known methods without such delivery method.

Thus, such application has a great interest for the treatment of cancer tumor. The drug is released by the delivery compound only inside the tumor. The cancer tumor may be treated without releasing the drug everywhere inside the body. The drug is often harmful and toxic for organs inside the body. Many undesirable side effects of a global treatment of the body may be therefore avoided.

Furthermore, the generation of ultrasound intensity is used for sonoporation or transfection applications, wherein plasmids are transferred inside a cell. For these applications, the substance comprises at least a plasmid. The substance may be a plasmid, a gene, or a plasmid graft on a liposome. The focal point P is positioned near at least one cell. The cavitation phenomenon releases the substance and simultaneously opens the cell to transfer the plasmid inside said cell.

For generating ultrasound intensity inside a region of interest of a medium, it is known to use a device which comprises a transducer to generate and to focus a single ultrasound beam on a target point inside a medium, so that to produce cavitation inside a region around said target point. This method is satisfactory, but still need to be improved.

In the document WO2008/018019, it is disclosed a device which comprises two transducers generating two ultrasound beams which are focused. However, the position of the transducers and the signals sent to the transducers are not optimized. The beams are not accurately superposed on the acoustic transducers focal points.

Indeed, it is important to take into account that each transducer has an acoustic focal distance that is a distance between the transducer surface and an acoustic focal point where the ultrasound pressure in the medium has the greatest amplitude. However, the transducers have a nonlinear behavior. The acoustic focal distance depends on the signal amplitude provided to the transducer, and, for example, the acoustic focal distance decreases for high amplitude signals.

The acoustic focal point of focused beam is the effective acoustic focal point, that is to say the point into the medium where a pressure reaches a maximum value, i.e. where the acoustical power or intensity inside the medium has a maximum value.

The transducers also have a geometric focal point. These geometric focal points are localized at a predetermined geometric focal distance from a surface of each transducer, said surface producing the ultrasound wave into the medium. The geometric focal point is defined by the geometrical properties of the transducer. For example, for a transducer having a semi-spherical surface, the geometric focal distance is substantially equal to the radius of curvature of said transducer's surface.

The acoustic focal point is located near the geometric focal point for a small amplitude signal provided to the transducer. Due to the nonlinear behavior of the transducer, this acoustical focal point is moving towards the transducer's surface with respect to increase of the signal amplitude.

A first transducer receiving a first signal of a first amplitude so that to generate a first beam of a first ultrasound wave inside a medium towards a first beam direction produces a first zone of high pressure inside said medium, i.e. a first zone of maximum acoustic power or intensity. The first zone is typically centered on the first acoustic focal point and has an elongated shape along the first beam direction. In case of a transducer having a frequency of 1 MHz, the first zone is for example a region of the medium having a length of 13 mm in the first beam direction and a width of 2 mm in orthogonal directions perpendicular to the first beam direction.

A second transducer receiving a second signal of a second amplitude so that to generate a second beam of a second ultrasound wave inside a medium towards a second beam direction produces a second zone of high pressure inside the medium, i.e. a second zone of maximum acoustic power or intensity. The second zone is substantially centered on the second acoustic focal point and has an elongated shape along the second beam direction. The second zone is similar to the first zone, and it has for example the same size as the first zone, but it is elongated in the second beam direction.

In case of a single beam focused on the acoustic focal point, the first zone corresponds to a region of the medium wherein the cavitation occurs if the first signal s1 has a first amplitude greater than a predetermined amplitude. This first zone is quite large and elongated. Moreover, the cavitation inside this region is not stable: cavitation bubbles appear and collapse at various positions inside the volume. These positions of the cavitation bubbles seem to move inside the region, and not to be equally spatially spread inside said region.

In case of non coaxial and confocal dual beams, the first and second zones intersect in a region of interest around the point on which the first and second acoustic focal points are superposed to each other, said region of interest having a reduced size compared to the size of said first zone or said second zone.

It is then difficult to accurately superpose the two acoustic focal points of two separate transducers (i.e. to focus the ultrasound beams generated by two transducers on a same focal point P) and more precisely to superpose them on a target point of the region of interest (i.e. to superpose the focal point P on the target point of the region of interest).

The transducers must be moved accordingly. Furthermore, for nonlinear transducers and/or nonlinear acoustic regimen, changing the amplitude of the signals influences or modifies the position of the acoustic focal points. Therefore, such tuning may be complex in practice.

BRIEF SUMMARY

The present invention overcomes the above detailed disadvantages by providing a method for determining optimized parameters of a device generating a plurality of ultrasound beams which are focused on a focal point P situated in a region of interest which can be a region inside a medium or a region at the interface between a first and a second fluid of the medium, said region of interest being reduced volume and size.

Thanks to the optimization of the parameters according to the method of the present invention, the at least one effect chosen amongst:

a cavitation effect localized inside the region of interest localized inside the medium, a single acoustic fountain effect localized in the region of interest which is at the interface between a first and a second fluid of the medium, a thermal increase effect localized inside the region of interest inside the medium, that occurs in said region of interest is more stable than the effect occurred without the optimization of the device generating localized ultrasound intensity.

A method is provided for determining optimized parameters of a device generating a plurality of ultrasound beams which are focused on a focal point P situated in a region of interest which can be a region inside a medium or a region at the interface between a first and a second fluid of the medium, so that said device produces around the focal point P inside the region of interest at least one effect chosen amongst:

a cavitation effect localized inside the region of interest localized inside the medium, a single acoustic fountain effect localized in the region of interest which is at the interface between a first and a second fluid of the medium, a thermal increase effect localized inside the region of interest inside the medium.

said method comprising the following steps:

a) providing a device which comprises:

at least two signal generators generating respectively a first signal s1 having an amplitude a1 and a second signal s2 having an amplitude a2, at least two ultrasound means, said at least ultrasound means being adapted respectively:

to receive the first signal s1 so that to generate a first beam B1 of a first ultrasound wave inside the medium towards a first beam direction D1, said first beam B1 being focused on a first acoustic focal point P1a inside said region of interest, to receive the second signal s2 so that to generate a second beam B2 of a second ultrasound wave inside the medium towards a second beam direction D2, said second beam B2 being focused on a second acoustic focal point P2a inside said region of interest, at least one means of detection of the at least one effect, b) positioning the at least two ultrasound means to each other so that the first and second directions D1,D2 are substantially coplanar and inclined relative to each other of an angle comprised between 60° and 120°, c) moving the at least two ultrasound means respectively of at least two displacements x1,x2 so that the at least one effect is detected inside the region of interest around the focal point P on which the first and second acoustic focal points P1a and P2a are superposed and not detected outside the region of interest, d) reducing the amplitude a1,a2 of the signals s1,s2 down to an amplitude level where the at least one effect is not detected, e) moving the at least two ultrasound means to a plurality of test positions, each of said test positions corresponding to said position of the ultrasound means wherein at least one of the ultrasound means has been moved by a displacement increment D, f) if the at least one effect is detected at one of the test positions at step e) around the focal point P on which the first and second acoustic focal points P1a and P2a are superposed, selecting said test position to be the position of the ultrasound means, and repeating steps d) and e), g) determining and recording the optimized parameters of the device which are the amplitudes a1,a2 of the signals s1,s2 and the position x1,x2 of the ultrasound means tuned before the last reduction at step d).

According to the method of the invention, the region which has a size in all directions lower than 5 mm, and preferably lower than 2 mm. The size of the region of interest depends on the frequencies of the ultrasound waves of the signals. If the frequencies are low, the focal zone is large. Indeed, the size of the focal zone is proportional to the wavelength.

The method according to the present invention is to provide specific and optimized parameters so as to have an effect inside a region of interest which can be an acoustic effect such that cavitation effect and such that all the acoustic focal points of the ultrasound means are superposed (i.e. the ultrasound beams are focused on a focal point P).

To this end, the first and second signals are tuned to have an amplitude that is minimum to generate the cavitation effect, and the ultrasound means must be also and simultaneously positioned to superpose all the acoustic focal points for that minimum amplitude of the signals. The cavitation effect is then localized inside the region of the medium, around the intersection point of the beams directions D1, D2 (i.e. around the superposition of the acoustic focal points). The cavitation effect is not localized outside of said region of interest.

The idea of the invention is that, for these optimized parameters:

a small change of the positions of the ultrasound means will cancel the effect; and a small reduction of the signals amplitude will cancel the effect in the region of a medium which can be an acoustic effect. In that case, the acoustic effect occurs only inside a region of interest that has a minimum size.

Thanks to the method according to the present invention, the region of interest has a reduced volume and size. The effect which can be an acoustic effect (i.e. a cavitation effect) is localized only inside the region of interest and not outside this region of interest. Moreover, the effect inside the region of interest is more stable.

The tests performed with a device as described above confirmed that the region of interest where the cavitation is produced is a small region having a size approximately of 2 mm×2 mm×2 mm in three orthogonal directions (X, Y, Z). Such region of interest having cavitation bubbles may be observed with an imaging transducer at a position relative to the device that is stable, not moving in time during. Inside said region of interest, the cavitation bubbles have in time during a constant density and are uniformly spread inside the region of interest. Outside said region of interest, no cavitation is observed.

Thanks to the method according to the present invention, the parameters (i.e. signals provided to the ultrasound means and positions of the ultrasound means to each other) are accurately tuned to superpose the acoustic focal points of the ultrasound means (i.e. to focused the ultrasound beams on a focal point P) so as to have an acoustic effect (e.g. a cavitation effect) inside a region around the intersection point and with minimum amplitude of the signals.

The cavitation effect is itself non-linear: it appears suddenly if the parameters are adequately tuned, and disappears suddenly if the parameters are not adequately tuned. Thanks to this behavior, an iterative method can be built to find the optimized best parameters values (signals and positions of the ultrasound means).

The at least two ultrasound means may be separated from each other. This is necessary to have a volume between them that is enough to place a test sample. For example, the ultrasound means are separated of a distance greater than 50 mm. This distance may be greater than 100 mm.

The device may comprise at least two displacement members that are adapted to move the at least two ultrasound means relative to each other, in particular to a position determined by the at least two displacements, said displacements being along different displacement directions.

In case, of two ultrasound means, the device only needs two displacements members to superpose the first and second acoustic focal points P1$a$, P2$a$. Generally, if the beams directions are coplanar, to superpose all the acoustic focal points, the device needs to comprise a number of displacement members that is equal to 2.(N−1), where N is the number of transducers.

According to the method of the invention, in step c), the displacements directions of the ultrasound means may be perpendicular to one of the beams directions.

Preferably, the ultrasound means are transducers. The transducers may be high intensity focused ultrasound (HIFU) transducers. Such transducers are able to generate high level of acoustical power, and are able to generate very small pressure and cavitation in the medium.

The means of detection of the at least one effect that comprises the device may be a sensor. For example, it may be a sensor that detects the cavitation effect inside the medium. The sensor may be an hydrophone sensor, a piezoelectric sensor, a fiber optic hydrophone sensor, a camera sensor, or any type of known sensor adapted to detect the cavitation.

According to an embodiment of the method of the present invention, the steps b) to g) may be executed by a control unit that comprises the device. The control unit may take into account a plurality of various factors that may influence the values of the predetermined optimized parameters or predetermined focal distances. For example, the factor may be the nature of the medium, the temperature of the medium, the temperature of the transducer.

The medium may be heterogeneous and its nature may vary. For example, if the medium is a body, it comprises bones and tissues of different nature. The different beams can be attenuated and defocused in a different ways as a consequence of this heterogeneity of the medium. This may result in a change of the superposition of the focal acoustic points that may to be taken into account.

Thus, the method of the invention may comprise a further step that takes into account the attenuation of the ultrasound beams and the variation of the sound speed along the ultrasound beams. More precisely, the method may comprise a further step of calculating:

the attenuation coefficient of each of the ultrasound beams, and the variation of the sound speed of each of the ultrasound beams, so that to take them into account for superposing the acoustic focal points on a same focal point P.

The device may further comprise an imaging means that images the medium to determine the region of interest inside the medium. This imaging means may be a third ultrasound means adapted to produce acoustic images of the medium. The third ultrasound means produces an image of the medium to define a region of interest inside said medium. The images produced with the imaging transducer are used to visualize the medium and to localize the cavitation bubbles inside the medium. These images may be used to determine the first and second signal amplitudes to control the cavitation level, in such a way as a closed controlled loop. The imaging transducer may be a transducer having a nominal frequency of 5 MHz and a comprising multi-element array of piezoelectric elements.

The device may further comprise a control means to move sequentially the focal point P to a plurality of determined points inside said region of interest so that to control the effect (for example the cavitation) inside said region of interest. Each determined point inside the region of interest may be controlled with a predetermined elapsed time or predetermined intensity of said first and second beams.

Thus, in an embodiment of the invention, before the step b), the method comprises a further step of imaging the medium to determine the region of interest inside the medium.

Moreover, the method of invention maybe carried out for focusing the ultrasound beams on a plurality of determined points (i.e. a plurality of target points) inside the region of interest by moving sequentially the focal point P to this plurality of determined points.

In other words, in an embodiment of the invention, the at least two ultrasound means may be moved to sequentially move the superposed acoustic focal points P1$a$, P2$a$ to a plurality of predetermined target points inside the region of interest inside the medium. The region of interest may be determined by an image produced by the imaging transducer.

In another embodiment of the invention, if the device comprises displacement members, the displacement members may move the ultrasound means to sequentially move the superposed acoustic focal points P1$a$, P2$a$ to a plurality of predetermined target points inside a region of interest inside the medium. The region of interest may be determined by an image produced by the imaging transducer.

It is well understood that the acoustic focal points P1$a$, P2$a$ may be moved by moving the first and second ultrasound means (transducers) relative to the medium or by moving the medium relative to the ultrasound means.

The control unit of the device may comprise additional mechanical devices to move the medium or a portion of the medium relative to the ultrasound means. For example, the mechanical devices may comprise displacement drives according to one, two or a plurality of linear directions or one, two or another plurality of rotational directions, or any combination of linear or rotational directions. For example, the mechanical devices comprise three displacement drives according to three orthogonal directions X, Y, Z.

Alternatively the ultrasound means may be able to produce a moveable beam of ultrasound wave, having a beam focused to a focal point having a controlled position inside the medium, without moving any mechanical parts. Such technique is well known and use beam forming technology with an ultrasound mean having a plurality of transducers, each of them precisely controlled according a beam forming algorithm.

In other embodiments, the device may comprise more than two ultrasound means to generate a plurality of beams intersecting whose acoustic focal points intersect on a focal point P localized inside the region of interest. The region has therefore a more reduced size and the cavitation inside this region is increased and more stable.

The angle α may be comprised between 60° and 120°. According to the performed experiments, this range of angle gives the most reduced size of region of interest. For a range of angle between 90° and 110° the inventors discovered that the crossing of first and second beams B1, B2 additionally generates an interference phenomenon that seems to stabilize the position of the cavitation bubbles inside the region of interest. Such range is preferred.

A reduced angle may be useful to have more than two ultrasound means in the device, to define a more precise shape of the region of interest, to reduce the size of the region of interest and to better stabilize the bubbles inside said region of interest.

In an embodiment of the invention, the angle $\alpha$ may be varied during the carrying out of the method. More precisely, the method of the invention may comprise a further step of varying the angle between the beam directions. This step of varying of the angle may be carried out after the step g) and before repeating the steps c) to g) until determining the most optimized parameters of the device.

This has the following advantages:
- to define more accurately around the target point a region of interest in which the at least one effect occurs, said region of interest being smallest and more stable.
- to be a solution for overcoming the problems of attenuation of the ultrasound beams and the variation of the sound speed along the ultrasound beams in case of a heterogeneous medium which are detailed above.

Indeed, it may be particularly advantageous to adapt the angle $\alpha$ according to the nature of medium so that to avoid as far as possible this attenuation and this variation of sound speed. Thus, the optimized parameters are more precisely defined thanks to the variation of the angle.

The first signal s1 has an amplitude tuned so that the first beam does not induce the cavitation near the acoustic focal point P1$a$ in the absence of the second beam. Reciprocally, the second signal s2 has an amplitude tuned so that the second beam does not induce the cavitation near the acoustic focal point P2$a$ in the absence of the first beam. But, the amplitude of the first and second signals are tuned so that to induce the cavitation inside the region of interest around the superposed acoustic focal points P1$a$, P2$a$, when both beams are present or at least when both of the first and second waves arrive inside said region of interest of the medium.

The first and second signals may comprise same or different frequencies, to respectively produce first and second ultrasound waves. Usually, the signals and waves have main frequencies comprised between 100 kHz and 10 MHz. Preferably, these frequencies are comprised between 0.2 MHz and 1.5 MHz.

The first signal s1 and the second signal s2 may be time continuous signals, or burst signals or a combination of continuous and burst sine signals. These signals comprise for example a sine wave or a plurality of sine waves or any other wave.

In case of first and second burst signals, the control unit that may comprise the device synchronizes these first and second signals so that the first and second waves arrive near the point on which the first and second acoustic focal points are superposed (i.e. the focal point P) at the same time. The waves add their amplitudes. The local pressure amplitude (acoustic power or intensity) may be increased.

The first and second signals may have equal amplitudes. The method of the invention is therefore easier to implement.

The amplitudes a1,a2 of the first and second signals s1,s2 can be defined by many different mathematical formulas. If a1 is the amplitude of the first signal s1, and if a2 is the amplitude of the second signal s2, the amplitude a of both signals can be defined by the following formula (I):

$$a=[(a_1^2+a_2^2)/2]^{1/2} \qquad (I)$$

Every known method for norming, equalizing the signals can be applied to define an amplitude of the first and second signals. These definitions can also be applied to an unlimited number of signals.

The method according to the present invention may be refined by implementing an iterative process at step d). The amplitudes a1,a2 of the signals s1,s2 provided to the ultrasound means is reduced step by step by the iterative process, wherein at each loop the amplitude is updated by the following formula (II):

$$\text{amplitude}=\text{amplitude}/k \text{ and } 1<k<2 \qquad (II)$$

where k is a reduction factor for decreasing the amplitude of the signals. The reduction factor may be lower than 1.5, and preferably lower than 1.1. The determined amplitude of the signals is therefore accurate.

Thus, the step b) is implemented by an iterative process, wherein the amplitude of the signals is reduced at each loop by a division of the previous amplitude with a reduction factor k having a value comprised between one and two, said loop being repeated until the at least one effect is not detected.

The optimized parameters can be predetermined, for example with experiments on the device, and directly stored inside a memory of the control unit that comprises the device.

The optimized parameters can be determined via predetermined focal distances of an ultrasound means for a plurality of signal amplitude provided to said ultrasound means. The focal distances of both first and second ultrasound means may be stored into the memory.

The optimized parameters can be determined from a mathematical model of the focal distance of an ultrasound means versus amplitude of a signal provided to said ultrasound means that comprises the device.

A test position may correspond to the previous position of the transducers x1, x2 wherein only one or any combination of the first or second displacements is increased or reduced by the displacement increment D.

For example, if the first displacement of the test position is denoted by x1', and if the second displacement of the test position is denoted by x2', we can have any combination of:

$$x1'=x1+D;$$

$$x1'=x1-D;$$

$$x2'=x2+D;$$

$$x2'=x2-D$$

These test positions enable to test if there is an acoustic effect at any position around the last or previous ultrasound means position. This is a search procedure of optimal position, executed for a new amplitude at each loop of steps d) and e).

Therefore, the method according to the invention is searching the optimal parameters that produce the localized ultrasound intensity inside a region of a medium or at the interface between a first and a second fluid of the medium for the minimal amplitude of the signals. This search method is executed with real signals and displacements of the ultrasound means and is therefore very accurate.

The method according to the present invention may be refined in doing between step f) and g) a step wherein: if the displacement increment D is not lower or equal than a minimum displacement increment Dmin, the displacement increment D is reduced and the steps d) and e) of the method are repeated. Thanks to this feature, a more accurate optimal test position of the first and second ultrasound means (more accurate values of the first and second displacements x1, x2 can be determined. Said minimum displacement increment Dmin may be equal to 0.1 mm, and preferably equal to 0.05 mm. The displacement increment D may be equal to 0.5 mm, and preferably equal to 0.1 mm. The determined test position is therefore accurate.

According to the method of the invention, the effect may be a thermal effect localized inside the region of interest inside the medium. The thermal effect can be detected and/or measured by a thermal sensor, such a thermal camera sensor, or a temperature sensible material. For example, a sheet of absorbent material that changes its color locally in response to a local change of temperature can be used. Such material can be used at the surface S or in the plane of the beams, and eventually in combination with an optical camera. The thermal effect is a local increase of temperature, for example during a specific duration.

Thus, the device disclosed above and the method according to the invention may be used for thermoablation or thermal treatment inside an in-vitro or in-vivo medium. Such hyperthermia is well used for cancer treatment.

The method of the invention improves the hyperthermia, as the treated region of interest has a more reduced size.

Such thermal increase can easily be detected. Indeed, a change of temperature can be determined in comparison to previous temperature values, or to a mean value. A relevant change of temperature due to ultrasound intensity concentrated inside the region of interest can be greater than a threshold, e.g. a threshold of 1° C. or 0.5° C.

The local thermal increase at the acoustic focal points is then used to determine experimentally the exact position of the acoustic focal points P1$a$, P2$a$, and to implement the method of the invention.

The thermal effect has the advantage of a more accurate superposition of the acoustic focal points. Indeed, the heating of the medium is linked to the positive part of the ultrasound wave. In case of non-linear regimen, the positive part of the ultrasound wave contains very high frequencies ("shocked waves") which are concentrated on the focal point P. Indeed, the size of the focal zone is proportional to the wavelength.

According to the method of the invention, the effect may be a single acoustic fountain effect at the interface between a first and a second fluid of the medium.

More precisely, each of the first and second beams B1, B2, generates acoustic radiation pressure inside the medium. Each acoustic radiation pressure may generate an acoustic effect at the liquid surface, called the acoustic fountain. Some droplets of liquid can be projected into air above the fluid surface from the interface points, respectively the first interface point A1 and the second interface point A2.

A single acoustic fountain occurs in case of a specific liquid level for which both acoustic fountains are superposed: only one acoustic fountain is visible.

This acoustic fountain effect can be used to determine the exact position of the first and second interface points A1, A2, that is to say the positions of the first and second beams B1, B2.

This acoustic fountain effect can easily be detected by an optical sensor, e.g. a camera sensor. This can be used to determine the exact position of the first and second interface points A1, A2, that is to say the positions of the first and second beams B1, B2 and the case in which the first and second interface points A1, A2 are superposed so that a single acoustic fountain effect occurs. Furthermore, the control unit of the device may process the images from the camera to detect the acoustic fountain effect. Consequently, the general method of the invention can be applied using the acoustic fountain effect.

According to various aspects, the method of the invention is particularly adapted and more efficient for delivering a substance inside a medium, the substance being held by a delivery compound in a holding state. The substance and the delivery compound may be those disclosed above. For example, the delivery compound is chosen in the list of nanoparticles and a microparticules. In another embodiment, the delivery compound is chosen in the list of liposomes and micelles.

In another embodiment of the invention, the method of the invention is particularly adapted and more efficient for delivering a substance inside a region of interest of a medium without a delivery compound when there is cavitation inside said region of interest of the medium. Indeed, the substance may be sensitive to the cavitation. Thus, the delivery compound may be not necessary. The method of the invention may be used for delivering a substance inside a region of interest (i.e. a target point, for example inside a tumor) of the medium without any delivery compound. The use of delivery compound is not compulsory.

As explained above, the generating and focusing of a plurality of ultrasound beams on a point inside a region of interest inside a medium (i.e. a target point) produces cavitation inside the region of interest around said target point and makes a delivery compound to switch from a holding state in which the substance is held by the delivery compound, to a releasing state in which the substance is released by the delivery compound.

Thanks to the method of the invention which determines optimized parameters for the focusing of the ultrasound beams on a focal point P so that to induce a cavitation inside the region of interest, i.e. around the target point, this region of interest wherein the substance is released and delivered has a reduced volume and size. Moreover, the inventors have observed that the cavitation inside the region is more stable.

Thus, the method of the invention has the advantage that the quantity of drug injected inside the body is much smaller than the quantity for known methods.

In an embodiment of the invention, the method is used for delivering a substance that comprises at least a plasmid and the medium is an aqueous medium that comprises cells. Thus, the target point is positioned near at least one cell, so that the cavitation releases the substance and opens the one cell to transfer the plasmid inside said cell. The method of the invention may be used for sonoporation or transfection applications, wherein plasmids are transferred inside a cell. These applications are in-vitro applications.

The sonoporation may be in-vitro or in-vivo applications for delivering plasmids.

In another embodiment of the invention, the substance is a drug intended to be delivered to a tumor inside said medium. The target point is positioned inside said tumor.

In another embodiment of the invention, the device disclosed above and the method of the invention may be used for destroying fat cells or adipocytes, inside a body. The method of the invention may be used for delivering a substance that comprises at least a catalyst substance. The adipocytes destruction is improved by the combination of the cavitation and the catalyst effects of the catalyst substance.

The method of the invention may be an in-vivo or an in-vitro method. In case of in-vivo method, the medium may be a human or animal body. In case of in-vitro method, the medium may be an aqueous medium, in particular in which cells may be stored. The medium may be a culture medium, preferably a culture medium used for in-vitro experiments on substances of interest before the carrying out of the experiments in in-vivo conditions.

According to the present invention, the medium may be any medium that can propagate ultrasound waves. For example, the medium may be an aqueous medium. The medium may be a human or animal body. The medium may be also an aqueous medium enclosed inside a test tube or a test capsule or any test device. Therefore, the medium may be an in-vitro or an in-vivo medium.

Tests were conducted to verify the efficiency of the combination of the transfection method and the present method for delivering a substance. Surprisingly, the cavitation generated for delivering the substance is also able to open the cells to transfer plasmids into the cells and without destroying said cells.

The test was done on mice. Two injections were done on these mice with RL cells so that 24 days after injection they have two tumors, each having a volume of at least 1000 mm3.

The first tumor is insonified with dual confocal ultrasound beams as described above.

A substance siRNA Bcl2L1 comprising genes coupled to an Alexa Fluor is injected into the second tumor. The Alexa Fluor is an example of marker (fluorescence marker) adapted to detect the presence of siRNA added genes. The injected volume is 30 µl, and the substance concentration is of 7.5 µg/ml.

Then, the second tumor is also insonified with the same dual confocal ultrasound beams.

Both tumor are analyzed to detect intracellular fluorescence. The second tumor comprises 16% of fluorescent cells, that is to say 16% of transfected cells. Higher percentages may be obtained.

BRIEF DESCRIPTION OF THE DRAWINGS

Other features and advantages of the invention will be apparent from the following detailed description of embodiments given by way of non-limiting examples, with reference to the accompanying drawings. In the drawings.

DETAILED DESCRIPTION

Figure 1:
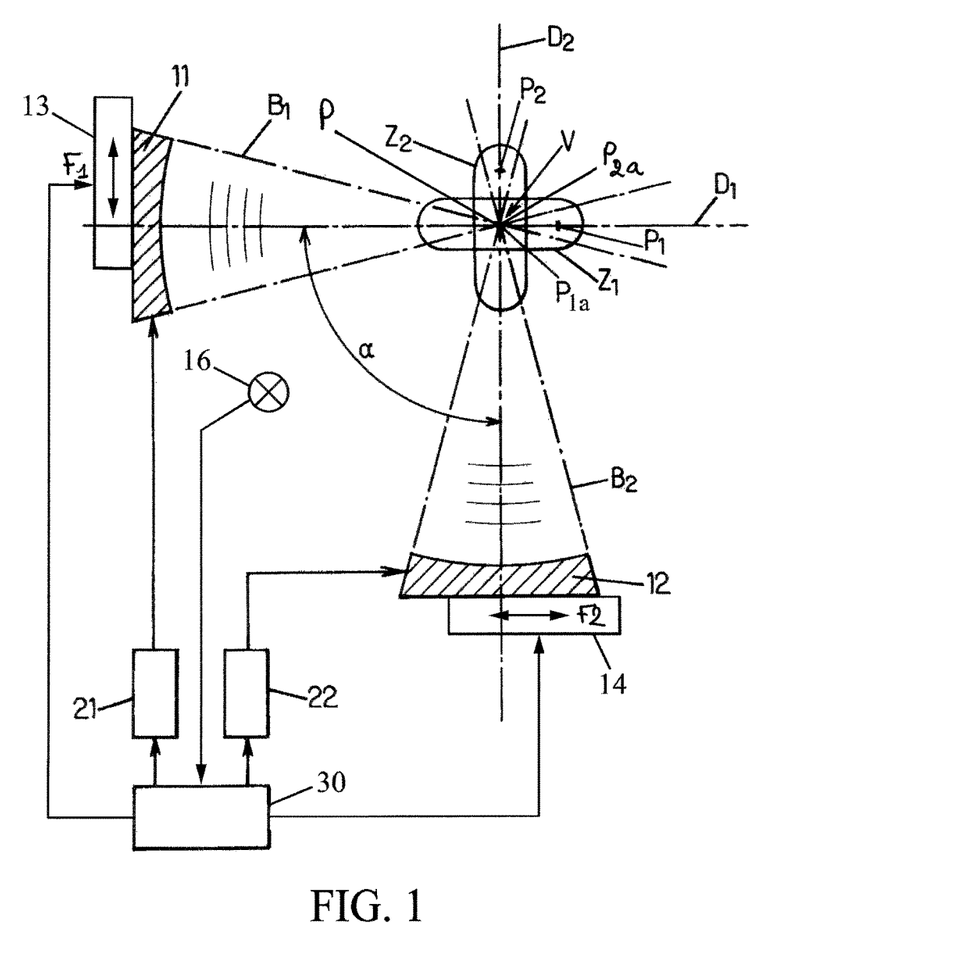
FIGS. 1 and 2 are schematic views of a device carrying out the method of the invention.

FIG. 1 represents a device 1 generating a localized ultrasound pressure. The device 1 comprises:
- a first ultrasound means 11 which is a transducer adapted to generate a first beam B1 of a first ultrasound wave inside the medium towards a first beam direction D1, said first beam B1 being focused to a first acoustic focal point P1a inside the medium (not shown),
- a second ultrasound means 12 (second transducer) adapted to generate a second beam B2 of a second ultrasound wave inside the medium towards a second beam direction D2, said second beam B2 being substantially focused on a second acoustic focal point P2a.
- a first and a second displacement members 13, 14 adapted to move the first and second transducers 11, 12 to a position determined by a first and second displacements x1, x2 of said respective first and second displacement members 13,14.

The first and second acoustic focal points P1a and P2a are superposed on a same point, the focal point P.

The first and second beams directions D1, D2 are substantially coplanar and inclined relative to each other of an angle α of 90°.

The first and second transducers 11, 12 are different transducers: They are not transducers elements integrated inside a single transducer. They are each driven by an independent signal to generate an independent ultrasound beam. The first transducer 11 receives a first signal s1 from a first signal generator 21 and generates the first beam B1. The second transducer 12 receives a second signal s2 from a second signal generator 22 and generates the second beam B2.

As shown in the FIG. 1, the geometric focal points P1, P2 are situated on the respective direction, first or second direction D1, D2, and they are situated at a distance from the transducer surface higher than the acoustic focal point P1a, P2a of the ultrasound beams B1, B2.

The first transducer 11 receiving a first signal s1 of a first amplitude also that to generate a first beam B1 of a first ultrasound wave inside a medium towards a first beam direction D1 produces a first zone Z1 of high pressure inside said medium, i.e. a first zone Z1 of maximum acoustic power or intensity. The first zone Z1 is substantially centered on the first acoustic focal point P1a and has an elongated shape along the first beam direction D1.

The second transducer 12 receiving a second signal s1 of a second amplitude a2 so that to generate a second beam B2 of a second ultrasound wave inside a medium towards a second beam direction D2 produces a second zone Z2 of high pressure inside the medium, i.e. a second zone of maximum acoustic power or intensity. The second zone Z2 is substantially centered on the second acoustic focal point P2a and has an elongated shape along the second beam direction D2.

The first and second zones Z1, Z2 intersect in a region of interest V around the focal point P on which the first and second acoustic focal points P1a, P2a are superposed to each other, said region of interest V having a reduced size compared to the size of said first zone Z1 or said second zone Z2.

The device 1 also comprises a control unit 30 adapted to control, synchronize and tune the characteristics of the first and second signal generators 21, 22. The control unit 30 is a computer with a keyboard, and a display for interfacing with a user. The control unit 30 provides the first and second signals s1, s2 to the first and second transducers 11, 12 respectively to generate the beams B1,B2. It also provides the first and second displacements x1, x2 to the first and second displacement members respectively to move the transducers 11,12. These first and second signals s1, s2 (mainly their respective amplitudes) and the first and second displacements x1, x2 are therefore parameters for tuning the device 1.

The device 1 further comprises a sensor 16 which is a camera.

Figure 2:
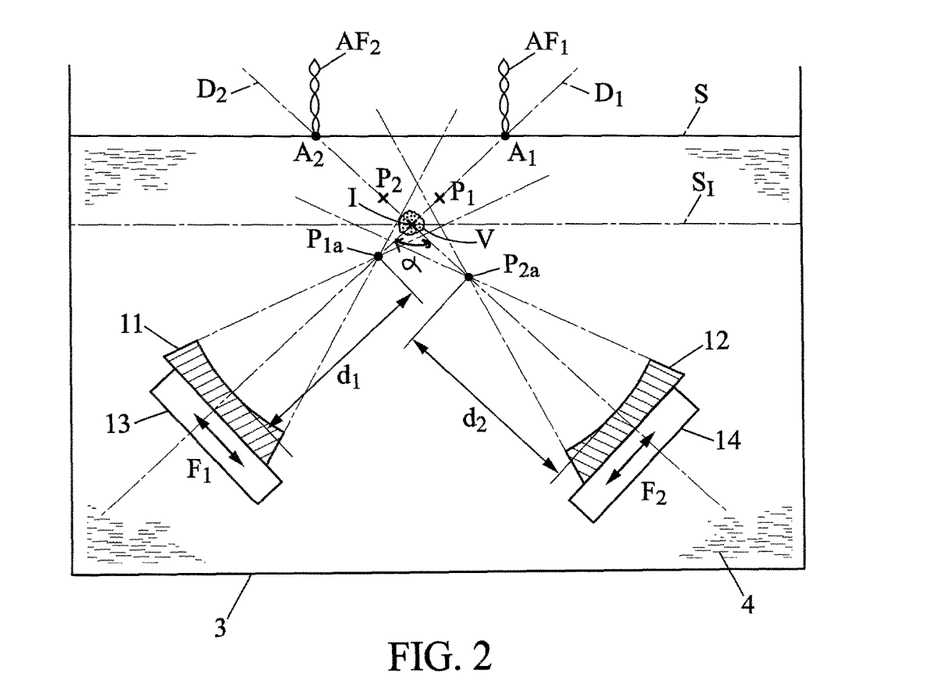

In the FIG. 2, the beams directions D1, D2 intersects each other at an intersection point I inside the medium. FIG. 2 shows a configuration of the device 1 that is not correctly tuned. The first and second acoustic focal points P1a, P2a are not superposed to each other and are not superposed on the intersection point I. But this FIG. 2 helps to understand how the device 1 is operated to superpose said acoustic focal points P1a, P2a.

As shown in the FIGS. 1 and 2, the first and second displacement members 13,14 support only one of the transducers 11, 12. The two displacement directions are represented by arrows F1 and F2 on the FIGS. 1 and 2. Moreover, the displacement directions F1,F2 are perpendicular to the beam directions D1, D2. More precisely, displacement direction F1 of the first displacement member 13 is perpendicular to the first beam direction D1, and the displacement direction F2 of the second displacement member 14 is perpendicular to the second beam direction D2.

On the FIG. 2, a first focal distance d1 of the first transducer 11 and a second focal distance d2 of the second transducer 12 are shown. The focal distance is the distance from the transducer surface to the acoustic focal point.

Around the intersection point I, a region of interest is virtually delimited on the FIG. 2. Inside the region of interest V, the first and second beams B1, B2 generate an acoustic effect inside said region of interest V; said acoustic effect is a cavitation effect.

On the FIG. 2, the medium 4 comprises a liquid having an upper surface S between said liquid and air. The liquid is contained inside a tank 3. The level of the liquid surface can be changed by liquid control means. For example, the level of the liquid can be lowered to a lower level. For example, the level of the liquid can be tuned to a specific level SI wherein the intersection point I is near or above said specific level SI of the liquid.

The first beam direction D1 intersects the surface S at a first interface point A1. Respectively, the second beam direction D2 intersects the surface S at a second interface point A2.

Each of the first and second beams B1, B2, generates acoustic radiation pressure inside the medium. Said acoustic radiation pressure may generate an acoustic effect at the liquid surface, called the acoustic fountain: Some droplets of liquid can be projected into air above the fluid surface S from the interface point. The first acoustic fountain AF1 and second acoustic fountain AF2 are represented on the FIG. 2. Such acoustic fountains can easily be detected by an optical sensor, e.g. a camera sensor.

This acoustic fountain effect can be used to determine the exact position of the first and second interface points A1, A2, that is to say the positions of the first and second beams B1, B2. The displacement members 13, 14 can therefore be actuated according to lateral directions so as the first and second beam directions are correctly coplanar.

In case, the liquid level is the specific level SI, both acoustic fountains are superposed: only one acoustic fountain is visible.

The acoustic fountain effect can then be used to determine experimentally the exact position of the intersection point I, and acoustic focal points.

The first and second focused beams B1, B2, also generate an increase of temperature at the acoustic focal points P1a, P2a (or very closed to these points).

Figure 3:
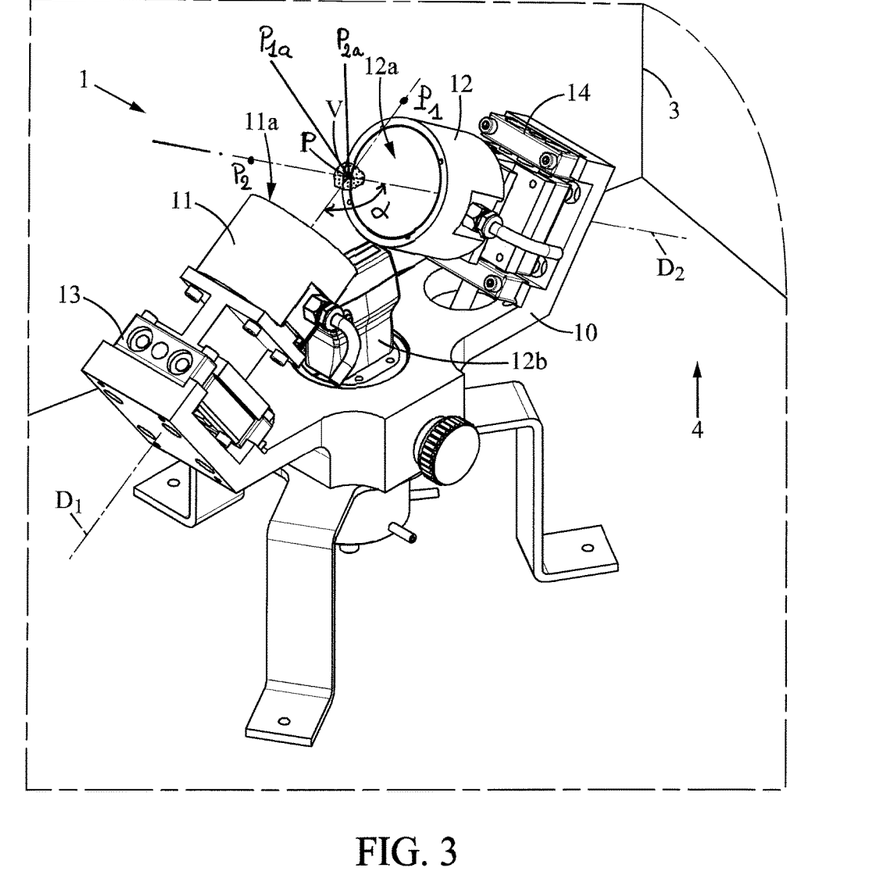
FIG. 3 is a perspective view of a device carrying out the method.

FIG. 3 shows an embodiment of the device 1 comprising first and second transducers 11, 12, first and second displacement members 13, 14, and support member 10.

FIG. 3 represents a device 1 comprising a water tank 3 filled with a medium 4 of degassed water. The degassed water is a medium having cavitation pressure levels equivalent to in vivo medium. It is therefore representative for tuning the parameters of the device. A non-degassed water would lead to lots of cavitation bubbles inside the medium, and inaccurate tuning of the device. In this device 1, the first ultrasound means comprises a spherical transducer 11 having an emitting surface 11a for emitting the first ultrasound wave in the first direction D1 and for focusing the first ultrasound wave at a first distance from the emitting surface 11a. The first transducer 11 is a piezoelectric ceramic transducer having a nominal frequency of 1 MHz, a first distance of 50 mm and an emitting surface 11a of 50 mm diameter.

The second ultrasound means comprises a second transducer 12 having an emitting surface 12a for emitting the second ultrasound wave in the second direction D2 and for focusing the second ultrasound wave at a second distance from the emitting surface 12a.

The second transducer 12 is identical to the first one. But, it can be different.

The first signal s1 is a pulsed burst sine wave of 1 MHz, with repetition frequency of 200 Hz, and a duty cycle of 5%. The first predetermined amplitude corresponds to a power of generated first ultrasound wave of 5 Watts.

In the embodiment of the device 1 shown in the FIG. 3, designed for testing the method of the invention, the angle a between the first direction D1 and the second direction D2 is 110°.

As shown in the FIG. 3, the geometric focal points P1, P2 are situated on the respective direction, first or second direction D1, D2, and they are situated at a distance from the transducer surface higher than the acoustic focal point P1a, P2a of the ultrasound beams B1, B2. The first and second acoustic focal points P1a and P2a are superposed on a same point, the focal point P.

The device 1 further comprises first and second displacement members 13, 14 adapted to move the first and second transducers 11, 12 to a position determined by a first and second displacements x1, x2 of said respective first and second displacement members 13,14.

The first displacement member 13 supports and is connected to the first transducer 11 for moving it according to a first displacement direction. Reciprocally, the second displacement member 14 supports and is connected to the second transducer 12 for moving it according to a second displacement direction. The first and second displacement members 13,14 move each transducer 11,12 independently to the other.

As shown in the FIG. 3, the device 1 comprises an imaging transducer 12b in order to produce images of the medium 4 around the intersection point P. The images produced with the imaging transducer 12b are used to visualize the medium 4 and to localize the cavitation bubbles inside the medium 4. These images are used to determine the first and second signal amplitudes to control the cavitation level, in such a way as a closed controlled loop. The imaging transducer 12b is a transducer having a nominal frequency of 5 MHz and a comprising multi-element array of piezoelectric elements.

Figure 4A:
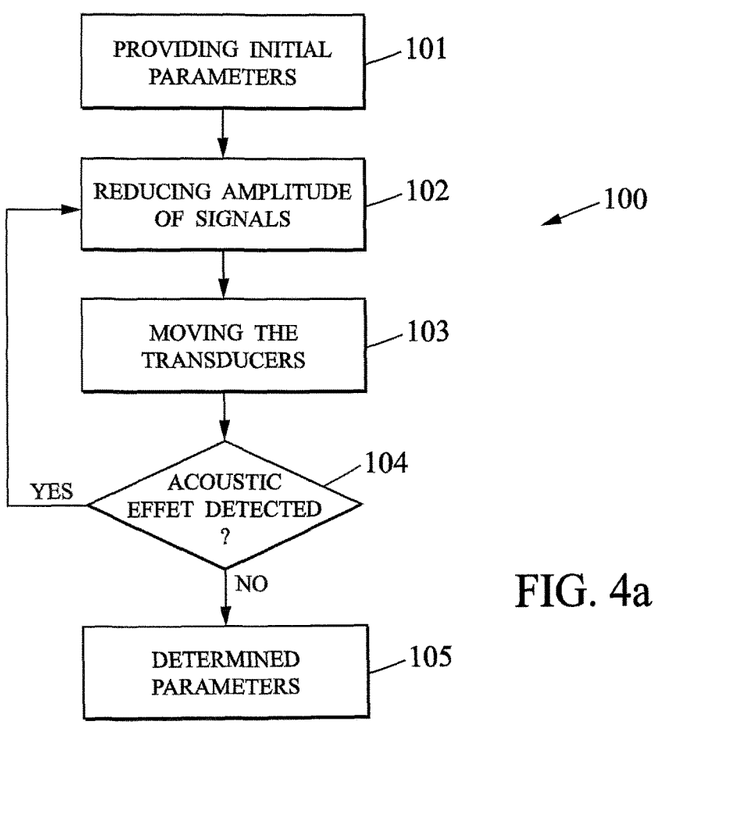
FIGS. 4a and 4b are flowcharts of an embodiment of the optimization method to determine the parameters according to the invention.

According to an embodiment of the device, the control unit 30 may determine the optimized parameters from an optimization process 100 illustrated on FIG. 4a and having the following optimization steps:

provide at step 101 initial parameters to move the first and second transducers by means of the first and second displacement members to a position and to generate first and second beams B1, B2 by means of said first and second transducers so that an acoustic effect is detected inside the medium, reducing at step 102 an amplitude of the signals down to an amplitude level where the acoustic effect is not detected, moving at step 103 the first and second transducers by means of the first and second displacement members to a plurality of test positions, each of said test positions corresponding to said position of the transducers wherein at least one of the first and second displacements is modified by a displacement increment (D), if the acoustic effect is detected at step 104 at one of the test positions at step c), selecting said test position to be the position of the transducers, and repeating steps b) and c) (steps 102 and 103), the determined parameters at step 105 are the signals and displacements tuned before the last reduction at step b).

Figure 4B:
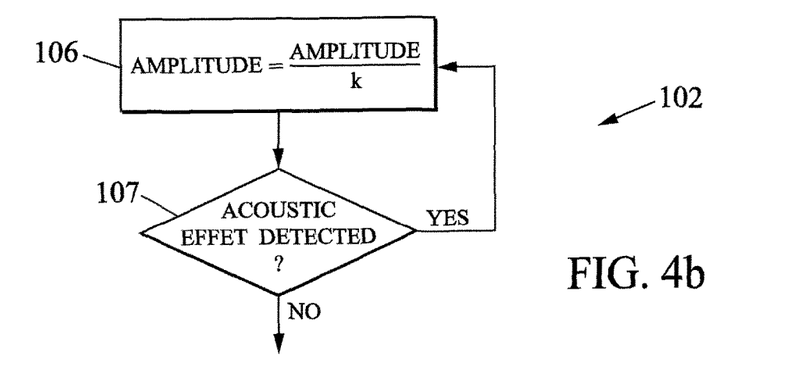

The above method may be refined by implementing an iterative process at step b) (step 102) represented on FIG. 4b.

The invention claimed is:

1. A method for setting a device generating a plurality of ultrasound beams which are focused on a focal point P situated in a region of interest which can be a region inside a medium or a region at an interface between a first and a second fluid of the medium, so that said device produces at least one effect around the focal point P inside the region of interest the at least one effect chosen amongst:
   a cavitation effect localised inside the region of interest localised inside the medium,
   a single acoustic fountain effect localised in the region of interest which is at the interface between a first and a second fluid of the medium,
   a thermal increase effect localised inside the region of interest inside the medium,
wherein said method comprises the following:
   a) providing a device which comprises:
      at least two signal generators generating respectively a first signal s1 having an amplitude a1 and a second signal s2 having an amplitude a2,
      at least two transducers, said at least two transducers being adapted respectively:
         to receive the first signal s1 so that to generate a first beam B1 of a first ultrasound wave inside the medium towards a first beam direction D1, said first beam B1 being focused on a first acoustic focal point P1a inside said region of interest,
         to receive the second signal s2 so that to generate a second beam B2 of a second ultrasound wave inside the medium towards a second beam direction D2, said second beam B2 being focused on a second acoustic focal point P2a inside said region of interest,
      at least two displacement members that are adapted to move respectively the at least two transducers independently relative to each other,
      at least one sensor for detection of the at least one effect,
   b) positioning the at least two transducers to each other so that the first and second beam directions D1, D2 are coplanar and inclined relative to each other at an angle a comprised between 60° and 120°,
   c) moving the at least two transducers independently relative to each other respectively of at least two displacements x1, x2 so that the at least one effect is detected inside the region of interest around the focal point P on which the first and second acoustic focal points P1a and P2a are superposed and not detected outside the region of interest,
wherein the method further comprises steps for determining optimized parameters for producing said at least one effect around the focal point P inside the region of interest:
   d) reducing the amplitude a1, a2 of the first and second signals s1, s2 down to an amplitude level where the at least one effect is not detected, the step d) being implemented by an iterative process, the amplitude of the signals being reduced at each loop by a division of a previous amplitude a1, a2 of the first and second signals s1, s2 with a reduction factor k having a value comprised between one and two, said loop being repeated until the at least one effect is not detected,
   e) moving the at least two transducers independently relative to each other to a plurality of test positions, each of said test positions corresponding to said position of the transducers wherein at least one of the transducers has been moved by a displacement increment D,
   f) if the at least one effect is detected at one of the test positions at step e) around the focal point P on which the first and second acoustic focal points P1a and P2a are superposed, selecting said test position to be the position of the transducers, and repeating steps d) and e),
   g) determining and recording the optimized parameters of the device which are the amplitudes a1, a2 of the signals s1, s2 and the position x1, x2 of the transducers tuned before a last reduction at step d), and
   h) updating settings of the device to correspond with the determined and recorded optimized parameters of the device.

2. The method according to claim 1, wherein the method is an in-vitro method and the medium is an aqueous medium in which cells are stored or a culture medium.

3. The method according to claim 1, wherein the region of interest has a size in all directions lower than 5 mm.

4. The method according to claim 1, wherein the device further comprises a means for imaging the medium to determine the region of interest inside the medium.

5. The method according to claim 1, wherein in step c), the transducers have displacements directions which are perpendicular to one of the first or second beams directions.

6. The method according to claim 1, wherein the device further comprises a control unit to move sequentially the focal point P to a plurality of determined points inside said region of interest so that to control the at least one effect inside said region of interest.

7. The method according to claim 1, wherein the method is carried out for focusing the ultrasound beams on a plurality of determined points inside the region of interest by moving sequentially the focal point P to this plurality of determined points.

8. The method according to claim 1, wherein the signals and waves have main frequencies comprised between 100 kHz and 10 MHz.

9. The method according to claim 1, wherein between step f) and g) a step wherein: if the displacement increment D is not lower or equal to a minimum displacement increment Dmin, the displacement increment D is reduced and the steps d) and e) of the method are repeated.

10. The method according to claim 1, wherein the method comprises a further step of varying the angle a.

11. The method according to claim 1, wherein the method is used for delivering a substance that comprises at least a plasmid and the medium is an aqueous medium that comprises cells.

12. The method according to claim 1, wherein the method is an in-vitro method and is used for sonoporation or transfection applications for transferring plasmids inside a cell.

13. The method according to claim 1, wherein the method is used for thermoablation or thermal treatment inside an in-vivo medium, which is a human or animal body.

14. The method according to claim 13, wherein the method is used for cancer treatment.

15. The method according to claim 1, wherein the method is used for in-vivo sonoporation for delivering plasmids.

16. The method according to claim 1, wherein the method is used for destroying fat cells or adipocytes, inside a body.

17. The method according to claim 16, wherein the method is used for delivering a substance that comprises at least a catalyst substance.

18. The method according to claim 1, wherein the method is used for delivering a substance inside an in-vivo medium, which is a human or animal body, the substance being held by a delivery compound in a holding state.

19. The method according to claim 18, wherein the delivery compound is chosen in the list of nanoparticles, microparticles, liposomes and micelles.

20. The method according to claim 18, wherein the substance is a radioactive substance, a color substance, a gene, aplasmide or a drug.

21. The method according to claim 1, wherein the method is used for delivering a substance inside an in-vivo medium without a delivery compound and wherein there is a cavitation inside the region of interest of the medium.

22. The method according to claim 1, wherein the medium is a tumor and the method is used for delivering a drug inside the tumor.

* * * * *